United States Patent [19]
Yamazaki

[11] Patent Number: 5,446,532
[45] Date of Patent: Aug. 29, 1995

[54] MEASURING APPARATUS WITH OPTICALLY CONJUGATE RADIATION FULCRUM AND IRRADIATED AREA

[75] Inventor: Tatsuya Yamazaki, Zushi, Japan

[73] Assignee: Canon Kabushiki Kaisha, Tokyo, Japan

[21] Appl. No.: 62,223

[22] Filed: May 18, 1993

[30] Foreign Application Priority Data

Jun. 9, 1992 [JP] Japan .................................. 4-149469

[51] Int. Cl.⁶ ............................................ G01N 21/00
[52] U.S. Cl. ........................................ 356/73; 356/338
[58] Field of Search .................. 359/434, 435; 356/73, 356/343, 338, 72

[56] References Cited

U.S. PATENT DOCUMENTS

| | | | |
|---|---|---|---|
| 4,942,586 | 7/1990 | Lai | 372/101 |
| 4,989,977 | 2/1991 | North, Jr. | 356/338 |
| 5,036,520 | 7/1991 | Bowman et al. | 372/101 |
| 5,048,050 | 9/1991 | Komurasaki | 372/101 |
| 5,055,265 | 10/1991 | Finlan | 356/445 |
| 5,093,838 | 3/1992 | Kubota | 372/101 |
| 5,198,369 | 3/1993 | Itoh et al. | 436/534 |

*Primary Examiner*—Richard A. Rosenberger
*Assistant Examiner*—Robert Kim
*Attorney, Agent, or Firm*—Fitzpatrick, Cella, Harper & Scinto

[57] ABSTRACT

A laser beam from a light source having a laser beam emitting portion and a laser output mirror is applied to an irradiation area in a flow cell by an irradiation optical system. Scattered light and fluorescence radiated by particles flowing through the flow cell are detected by a detector. The vicinity of the laser output mirror which is the fulcrum of the fluctuation of the pointing of the laser beam and the irradiation area are made optically substantially conjugate with each other, and even if the pointing of the laser beam fluctuates, measurement can be effected accurately without being affected thereby.

10 Claims, 5 Drawing Sheets

MEASURING APPARATUS WITH OPTICALLY CONJUGATE RADIATION FULCRUM AND IRRADIATED AREA

BACKGROUND OF THE INVENTION

1. Field of the Invention

This invention relates to a measuring apparatus for applying light, for example, to an object to be examined and measuring scattered light and fluorescence radiated from the object to be examined.

2. Related Background Art

Flow cytometers, particle counters, foreign substance defect inspecting apparatuses, etc. are known as examples of a measuring apparatus for applying a radiation beam such as a laser beam to an object to be examined and measuring scattered light and fluorescence radiated from the object to be examined, and have been widely used in the fields of biology, medical treatment, semiconductors and other industries.

Generally, in a precise optical measuring apparatus, a laser beam excellent in monochromatism and light condensing property is used as a light source. Usually, however, the pointing of the laser beam minutely fluctuates at a frequency of 100 Hz or more and at the same time, this pointing also fluctuates gently due to the heat contraction of a laser holding mechanism. Consequently, in the optical system of the prior-art measuring apparatus, accurate control of the applied position of the laser beam has been difficult and further improvement in measurement accuracy has not been easy.

Also, if a fluid system for flowing a particle is unstable, the particle flowing through a flow path will fluctuate from its original position in a direction orthogonal to the flow path. In this case, the intensity of the laser beam assumes Gaussian distribution and therefore, when the position of the particle fluctuates relative to the applied laser beam, the intensity of the laser beam applied to the particle changes and thus, the intensity of scattered light radiated from the particle or the fluorescence excited by the laser beam becomes unstable and accurate measurement of the particle becomes difficult.

So, in order to solve this problem, the spot shape of the applied laser beam has heretofore been made into an elliptical shape having a major axis in a direction orthogonal to the flow of the particle. Thus, the intensity distribution of the applied laser beam spreads and the variation in the intensity of the applied beam in a direction orthogonal to the flow decreases and therefore, even if the position of the particle somewhat moves in said direction relative to the applied laser beam, the fluctuation of the intensity of the applied laser beam impinging on the particle can be suppressed.

In this method, however, the cross-sectional area of the applied laser beam becomes large and therefore, the density of the light energy applied to the particle decreases and as a result, the intensities of scattered light and fluorescence radiated from the particle become weak and the S/N ratio of a signal detected by a detector becomes low. To compensate for this, a laser source emitting a powerful laser beam can be used, but this will lead to the bulkiness and increased cost of the apparatus.

SUMMARY OF THE INVENTION

It is the object of the present invention to provide a measuring apparatus which can accomplish accurate measurement irrespective of the fluctuation of the pointing of radiation energy without leading to the bulkiness and increased cost of the apparatus.

The measuring apparatus of the present invention which achieves this object has an energy radiation source, applying means for applying radiation energy from said energy radiation source to an object to be examined, and detecting means for detecting the characteristic of said object to be examined, and is characterized in that said applying means makes the fulcrum of the fluctuation of the pointing of said radiation energy and an irradiation area in which said object to be examined is irradiated with the radiation energy substantially conjugate with each other.

DESCRIPTION OF THE PREFERRED EMBODIMENTS

Figure 1:
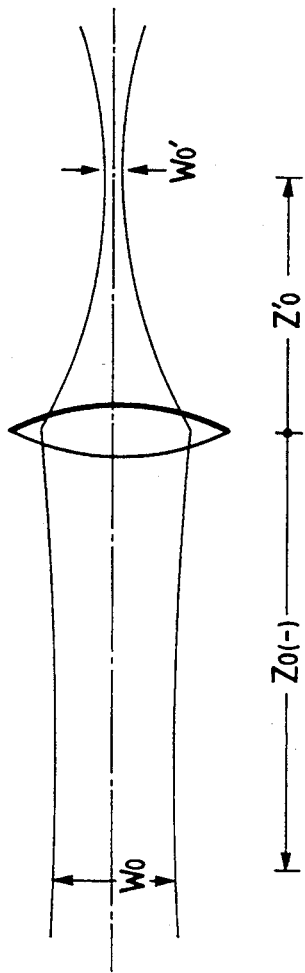
FIG. 1 is an illustration representing the imaged state of a laser beam (Gaussian beam).

In describing some embodiments of the present invention, description will first be made of the basic concept of the present invention. Generally, the diameter and position of the beam waist of a laser beam are expressed by the following equations (1) and (2) (see FIG. 1). In the following equations, $w_0$ is the diameter of the object side beam waist, $w_0'$ is the diameter of the image side beam waist, $z_0$ is the distance between the lens and the object side beam waist, $z_0'$ is the distance between the lens and the image side beam waist, f is the focal length of the lens, and $\lambda$ is the wavelength of the light.

$$w_0' = w_0 f / ((f+z_0)^2 + a^2)^{\frac{1}{2}} \tag{1}$$

$$z_0' = f(1 - f(f+z_0)/((f+z_0)^2 + a^2)) \tag{2}$$

$$a = \pi w_0^2 / \lambda$$

If in equation (2), the beam waist is at the object side focus position of the optical system, $z_0 = f$ and therefore, $$z_0' = f \tag{3}$$

and in whatever optical system, the beam waist occurs at the image side focus position. If an afocal system typified by a beam expander is used for this, the diameter $w_0'$ of the image side beam waist is expressed by the following equation (see FIG. 2). $f_1$ is the focal length of a first lens 33, and $f_2$ is the focal length of a second lens 34.

$$w_0' = w_0(f_2/f_1) \tag{4}$$

The image side focus position of the first lens 33 and the object side focus position of the second lens 34 are confocal dispositions which are the same positions and therefore, if from equation (2), the beam waist is placed at the object side focus position of the first lens 33, a beam waist expressed by equation (4) will occur at the image side focus position of the second lens 34.

Figure 2:
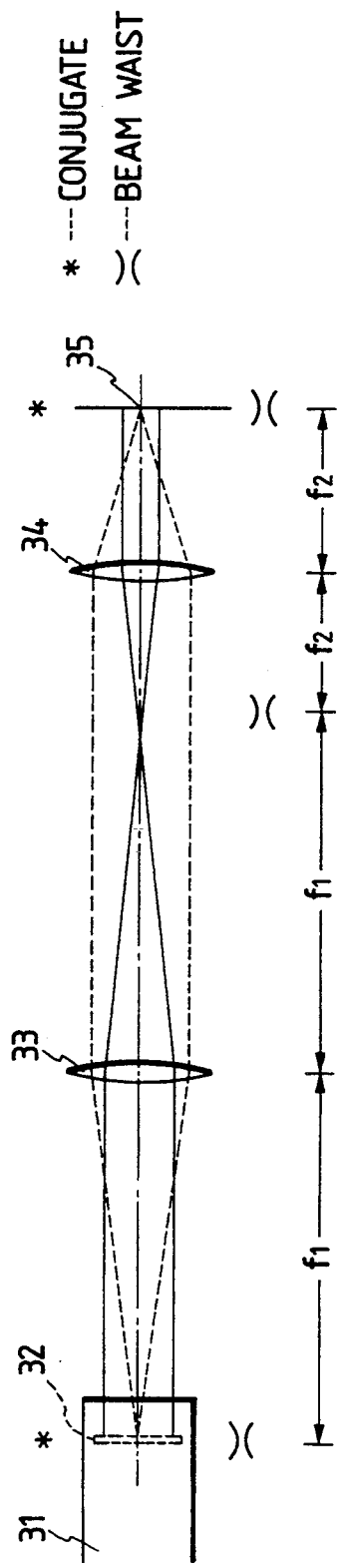
FIG. 2 is an illustration of an inclination correcting irradiation optical system.

On the other hand, as indicated by dotted lines in FIG. 2, the object side focus position of the first lens 33 and the image side focus position of the second lens 34 are conjugate with each other and therefore, a ray which has passed the object side focus position of the first lens 33 passes the image side focus position of the second lens 34 irrespective of the angle thereof.

Although it differs more or less depending on the disposition of a mirror constituting a laser resonator, it is known that generally a laser forms a beam waist near the output mirror thereof and therefore, if the output mirror 32 of the laser is placed at the object side focus position of the first lens 33 and an irradiation area 35 is placed at the image side focus position of the second lens, a beam waist will be formed in the irradiation area 35 without being defocused and the position of the laser beam entering the irradiation area 35 will not fluctuate irrespective of the angle at which the laser beam emerges from the output mirror 32.

As previously described, the pointing of a laser beam fluctuates minutely with time and the fluctuation of the directionality of particularly 100 Hz or more occurs with a laser output mirror as the fulcrum. Consequently, if the mirror and the irradiation area are made conjugate with each other, the applied spot position in the laser irradiation area will not fluctuate even if the pointing of the laser beam fluctuates. Also, the pointing of the laser beam is gently fluctuated by the heat contraction of a laser supporting mechanism, but the fulcrum of this fluctuation of the pointing often exists near the laser mirror and therefore, by the laser output mirror and the irradiation area being also made conjugate with each other, the fluctuation of the laser applied position can be suppressed. This irradiation optical system having the optical correcting function will hereinafter be called the "inclination correcting irradiation system".

EMBODIMENT 1

Figure 3:
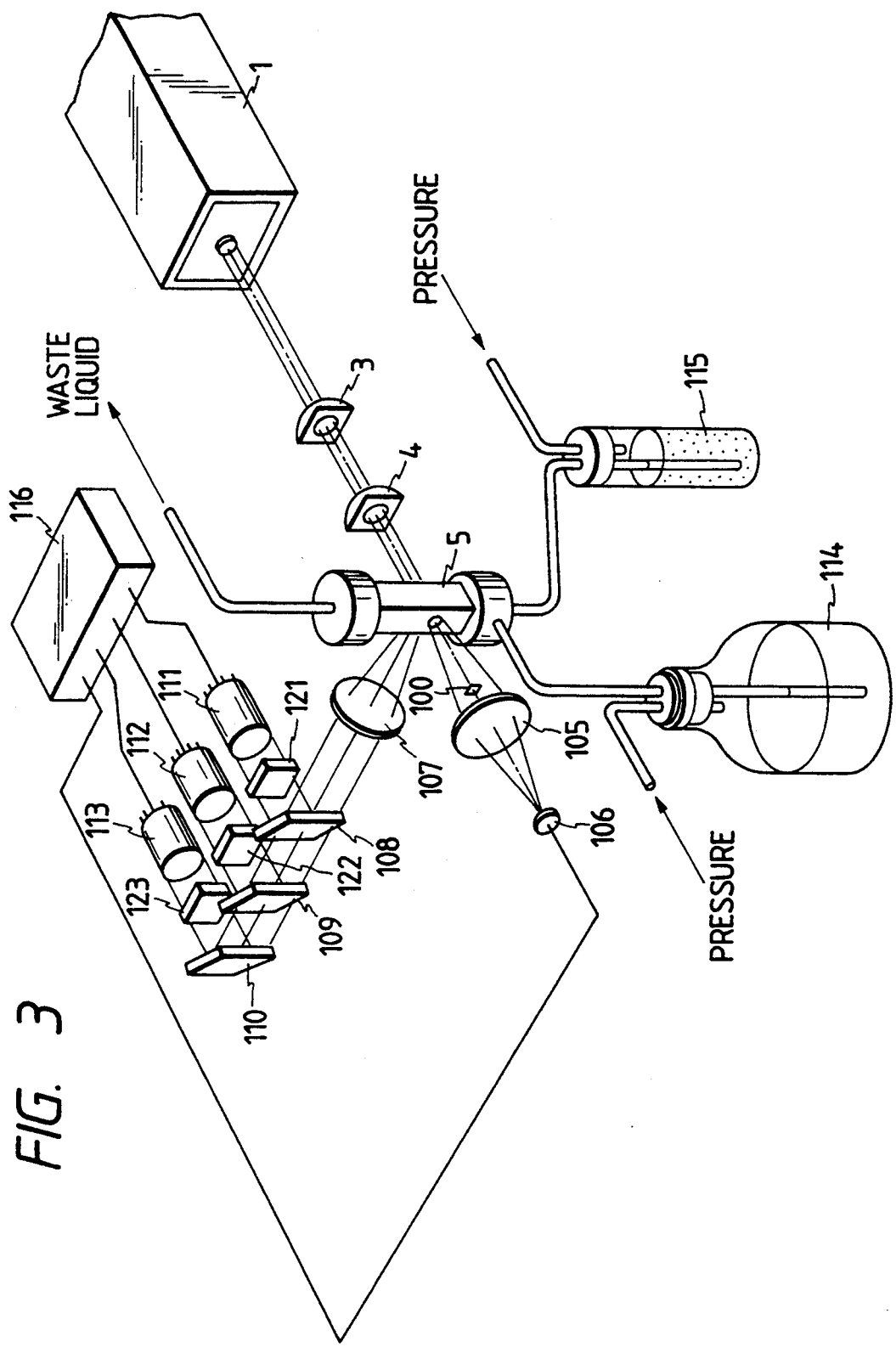
FIG. 3 shows the general construction of a flow cytometer.

A more specific embodiment will now be described. FIG. 3 shows the general construction of an embodiment in which the present invention is applied to a flow cytometer. Sample liquid such as blood is dyed with a fluorescent reagent as a preparation and is regulated to an appropriate reaction time and diluted concentration. This is then put into a sample liquid container 115. Also, sheath liquid such as distilled water or physiological salin solution is put into a sheath liquid container 114. The sample liquid container 115 and the sheath liquid container 114 each are pressurized by a pressurizing mechanism, not shown. Thereupon, in a flow cell 5, the sample liquid is wrapped in the sheath liquid and converged into a thin stream, and passes substantially the center of the flow path portion in the flow cell 5. At this time, individual particles (such as cells, microbes or carrier particles) wrapped in the sample liquid are separated and flow successively one by one. A laser beam emitter from a laser source unit 1 is applied to this flow of particles by an irradiation optical system having lenses 3 and 4. The irradiation optical system, as will be described later, makes the fulcrum of the fluctuation of the pointing of the laser beam emitted from the laser source unit 1 and the irradiated position of the flow cell optically conjugate with each other.

When the light beam is applied to the particles, scattered lights and fluorescence are radiated. Of the scattered lights, forward scattered light radiated in the forward direction of the optical path is metered by a detection system for forward scattered light comprising a condensing lens 105 and a photodetector 106. A light-absorbent minute stopper 100 is provided short of the condensing lens 105 in the optical path to prevent the applied light beam from directly entering the photodetector 106, so that the direct light from the irradiation light source and transmitted light transmitted through the particles may be eliminated. Thereby only the scattered light from the particles can be metered.

Also, light emitted from the irradiated particles in a lateral direction orthogonal to the optical axis of the laser and the flow of the particles is condensed by a condensing lens 107. A scattered light in such direction is called as side scattered light. The condensed light is reflected by a dichroic mirror 108 and passes through a band-pass filter 121 selectively transmitting therethrough the wavelength of the scattered light, i.e., the wavelength of the laser beam (in the case of an Ar+ laser, 488 nm) and the side scattered light is metered by a photodetector 111. Also, where the particles are fluorescence-dyed, of fluorescences condensed by the condensing lens 107 and transmitted through the dichroic mirror 108, green fluorescence is detected by a set of a dichroic mirror 109, a band-pass filter 122 for green fluorescence wavelength (in the vicinity of 530 nm) and a photodetector 112 to meter fluorescences of plural colors radiated with the scattered light, and the signals of a band-pass filter 123 for red fluorescence wavelength (in the vicinity of 570 nm) and photodetectors 106, 111, 112 and 113 are input to a calculation circuit 116, in which calculations such as the counting of the particles and the analysis of the kinds and properties of the particles are effected.

Figure 4:
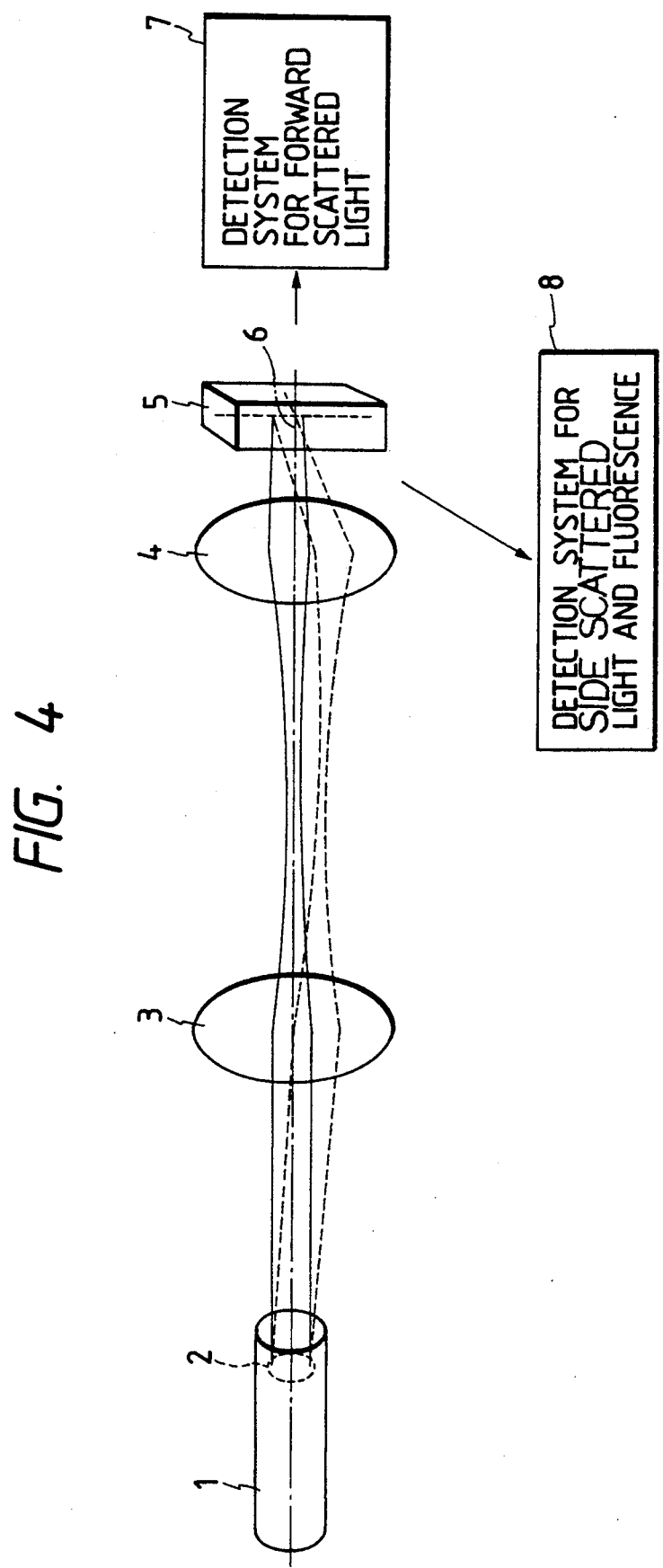
FIG. 4 shows the construction of a flow cytometer irradiation optical system according to a first embodiment of the present invention.

FIG. 4 shows the construction of the irradiation optical system of the present embodiment. The reference numeral 1 designates a laser emitting portion and the reference numeral 2 denotes a laser output mirror, and these together constitute a laser source unit. A laser beam emitted from the laser emitting portion 1 has its beam diameter changed by a beam compressor comprising a set of convex lenses 3 and 4 forming a confocal arrangement and is applied to an irradiation area 6 in a flow cell 5. Cells which are objects to be examined are individually flowing in the irradiation area 6, and radiate scattered lights and fluorescences conforming to the characteristics thereof by the applied laser beam. These are detected by a detection system 7 for forward scattered light and a detection system 8 for side scattered light and fluorescence.

In the irradiation optical system of the prior-art flow cytometer, the irradiation area has been located at the focus position of a condensing lens, that is, infinity and the irradiation area have been made conjugate with each other, and therefore, there has been the problem that the irradiation position will move if the pointing of the laser beam fluctuates, whereas the present embodiment is the aforedescribed inclination correcting irradiation optical system and therefore, the laser beam applied position in the flow cell is always kept constant and the fluctuation of the intensity of the irradiating light applied to the particles becomes null. Consequently, as compared with the prior art, the measurement of the quantities of scattered light and fluorescence can be effected more accurately. At the same time, for the reason already set forth, the beam waist can be accurately formed at the irradiation position without being defocused and therefore, the fluctuation of the beam diameter is minimized and the accurate measurement of the quantities of scattered light and fluorescence can be accomplished. That is, according to the present embodiment, the irradiation position is accurately controlled by the use of the inclination correcting irradiation optical system, whereby there is provided an optical measuring apparatus of very high accuracy.

EMBODIMENT 2

Figure 5A:
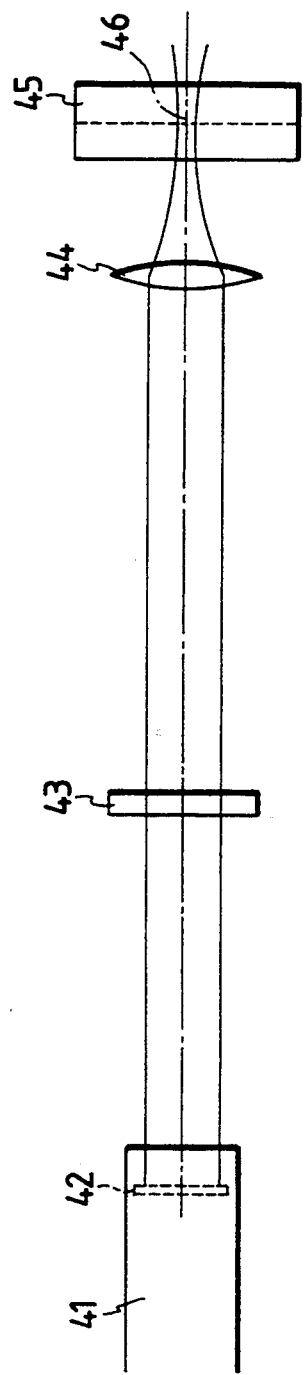
FIGS. 5A and 5B show the construction of an irradiation optical system according to a second embodiment of the present invention.
Figure 5B:
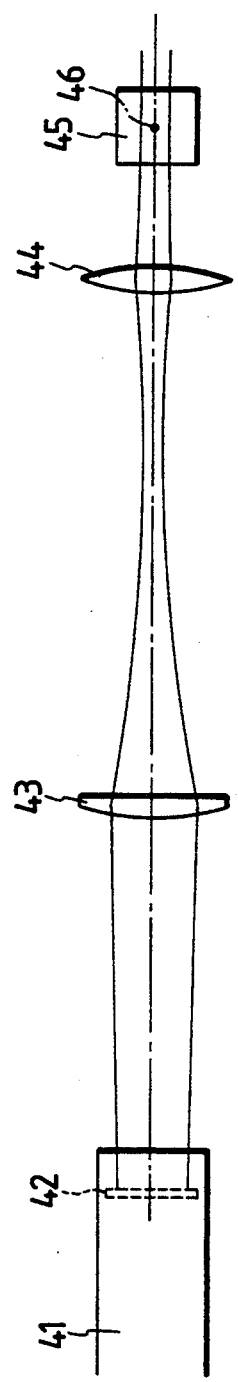

Description will now be made of a second embodiment which is a further improvement over the above-described embodiment. FIGS. 5A and 5B show the construction of an irradiation optical system according to the second embodiment, FIG. 5A being a cross-sectional view taken in parallel to the flow path of cells, and FIG. 5B being a cross-sectional view taken perpendicularly to the flow path of cells. In these figures, the reference numeral 41 designates a laser beam emitting portion, the reference numeral 42 denotes a laser output mirror, the reference numeral 43 designates a cylindrical lens of a meridional direction focal length $f_3 = 50$ mm, the reference numeral 44 denotes a convex lens of a focal length $f_4 = 20$ mm, the reference numeral 45 designates a flow cell, and the reference numeral 46 denotes an irradiation area. As is apparent from these figures, the present embodiment constitutes an anamorphic optical system and therefore will be described by each cross-section.

In FIG. 5A, a laser beam emitted from the laser beam emitting portion 41 through the laser output mirror 42 is rectilinearly transmitted through the cylindrical lens 43 having no power in this direction and is condensed on the irradiation area 46 in the flow cell 45 by the convex lens 44. When the diameter of the laser beam in the laser output mirror 42 is $d_1 = 1$ mm, the diameter $d_2$ of the laser beam in a direction parallel to the flow path in the irradiation area is expressed by the following equation, where the wavelength $\lambda = 488$ nm.

$$d_2 = 4\lambda f_4/(\pi d_1) = 12.4 \ (\mu m) \quad (5)$$

On the other hand in FIG. 5B, a laser beam emitted also from the laser beam emitting portion 41 through the laser output mirror 42 has its beam diameter changed by the cylindrical lens 43 and convex lens 44 constituting a beam compressor and enters the irradiation area 46. The diameter $d_3$ of the laser beam in a direction orthogonal to the flow path in the irradiation area 46 can be calculated from equation (4).

$$d_3 = 40 \ (\mu m)$$

Measurement accuracy will now be considered. In the cross-section of FIG. 5A, it is the convex lens 44 alone that has power, and the irradiation area 46 is disposed at the focus position of the convex lens 44 and therefore, when the directionality of the laser fluctuates, the irradiation position of the laser moves along the flow path. However, cells are also moving along the flow path and therefore, the fluctuation of the irradiation position in the direction of the flow path has nothing to do with the stability of the measured value.

On the other hand, in a direction orthogonal to the flow path, the fluctuation of the irradiation position brings about a variation in the measured value, as previously described, but since the cross-section of FIG. 5B constitutes an inclination correcting irradiation system as in the first embodiment, the stability of the irradiation position is realized in this direction. Moreover, $d_2 < d_3$ and therefore, even if the stability of the flow path position is more or less low, the measured value can be stabilized relatively.

Now, generally, in a flow cytometer, two cylindrical lenses, a beam diameter changing prism, etc. are used to make laser irradiation light into an elliptical shape and the aspect ratio of the laser beam diameter, i.e., the ratio between $d_2$ and $d_3$, is of the order of 1 to 10, but in the present embodiment, even the order of 1 to 3.2 is sufficient, and the reduction in the energy density of the applied laser beam is suppressed and yet highly accurate measurement free of the fluctuation of the irradiation position is realized. Accordingly, an expensive powerful laser is unnecessary. Usually, a cylindrical lens is difficult and expensive to manufacture and is generally made into a plano-convex lens having one surface thereof made flat and therefore, aberrations cannot sometimes be sufficiently corrected particularly by a lens of a short focal length. In the present embodiment, however, a long focus cylindrical lens and a short focus biconvex spherical lens are used to thereby curtail the number of cylindrical lenses, and this leads to the merit that costs are reduced and the imaging performance can be improved. Also, if said short focus biconvex spherical lens is substituted for by an achromatic lens like a microscope objective lens, countermeasure will become easy also when the wavelength of the light source is changed.

As described above, in the measuring apparatus wherein the object to be examined flows along the flow path, the inclination correcting optical system is adopted in the direction orthogonal to the flow path, whereby the variation in the quantity of light in the irradiation area can be reduced and accurate measurement can be realized without the use of a large laser.

EMBODIMENT 3

In the second embodiment, in the measuring apparatus wherein the object to be examined flows along the flow path, the inclination correcting irradiation system is adopted in the direction orthogonal to the flow path to thereby realize highly accurate measurement, while in a third embodiment, the alignment of the laser beam application position is further improved.

The laminar flow system adopted in a flow cytometer is a technique excellent in letting an object to be examined such as a cell flow stably and accurately, but through which location in the flow cell the object to be examined flows cannot be seen until the object to be examined is let flow. This leads to the problem that the adjustment of the alignment cannot be accomplished by an optical system alone and the final adjustment of the alignment cannot be done until actually the object to be examined begins to flow. Against this problem, as seen in U.S. Pat. No. 4,989,977, a glass plate or the like has heretofore been provided between the irradiation optical system and the irradiation area and it has been inclined to thereby effect the final alignment of the laser beam application position. In this method, however, the glass plate is placed at a location whereat the irradiating light is not parallel and therefore, not only aberrations occur and an accurate spot is not obtained, but also a ghost image is created by the glass plate and wrong measurement is effected. Further, the irradiation position sensitively reacts to the inclination of the glass plate and therefore, minute adjustment is difficult. Also, when a minute laser spot is necessary at the irradiation position, the focal length of the irradiation optical system becomes short and the spacing between the irradiation optical system and the irradiation area becomes narrow and therefore, in some cases, it becomes difficult to place the glass plate between the two.

So, in the present embodiment, the irradiation optical system is constructed so that the vicinity of the laser output mirror and the irradiation area may become conjugate with each other, and variable optical path displacing means is provided between the laser output mirror and the irradiation optical system, whereby the alignment of the laser beam application position is effected highly accurately.

Figure 6A:
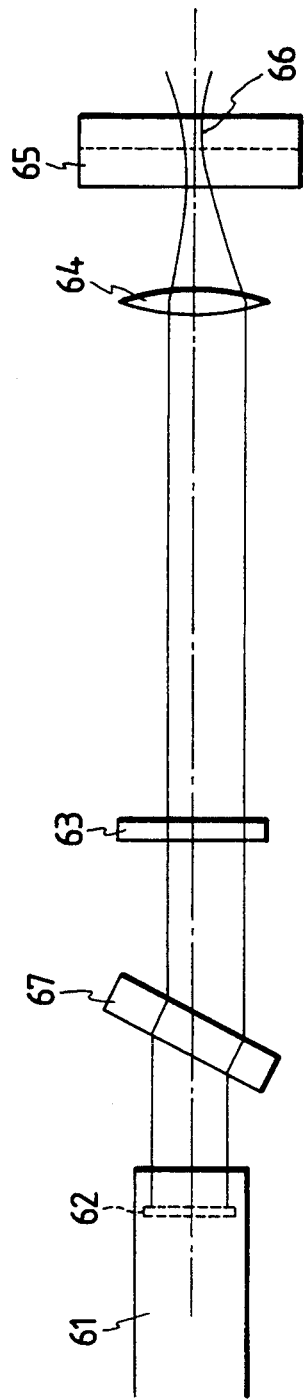
FIGS. 6A and 6B show the construction of an irradiation optical system according to a third embodiment of the present invention.
Figure 6B:
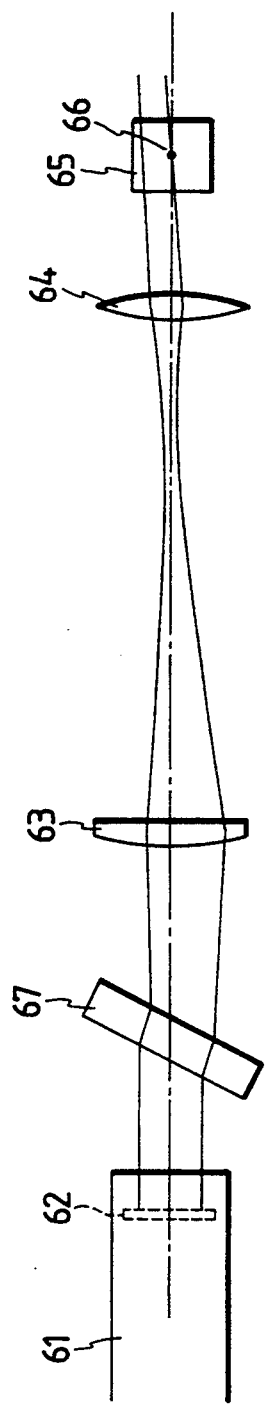

The third embodiment will hereinafter be described with reference to the drawings. FIGS. 6A and 6B show an optical system in which the present invention is applied to the irradiation optical system of a flow cytometer, and as in the second embodiment, FIG. 6A is a cross-sectional view taken in parallel to the flow path of cells, and FIG. 6B is a cross-sectional view taken perpendicularly to the flow path of cells. In these figures, the reference numeral 61 designates a laser beam emitting portion, the reference numeral 62 denotes a laser output mirror, the reference numeral 63 designates a cylindrical lens of a meridian direction focal length $f_3 = 50$ mm, the reference numeral 64 denotes a convex lens of a focal length $f_4 = 20$ mm, the reference numeral 65 designates a flow cell, the reference numeral 66 denotes an irradiation area, and the reference numeral 67 designates a plane parallel plate. Except for the plane parallel plate 67, this embodiment is the same in construction as the second embodiment and therefore, the duplicate portions need not be described.

Here, description will be made of the effect when the plane parallel plate 67 of a variable angle is inserted between the laser output mirror 62 and the cylindrical lens 63 as shown in FIGS. 6A and 6B. First, in the cross-section parallel to the flow path, i.e., FIG. 6B, the plane parallel plate 67 is inserted in a portion wherein the laser beam is substantially parallel, and the convex lens 64 alone is a lens having power and the irradiation area 66 and infinity are conjugate with each other through the lens 64 and therefore, even if the angle of the plane parallel plate 67 is changed, the angle of the laser beam at the irradiation position will vary, but the laser beam application position will not move within a range in which the aberrations of the convex lens 64 can be neglected. On the other hand, in the cross-section perpendicular to the flow path, i.e., FIG. 6A, the plane parallel plate 67 is inserted also in a portion wherein the laser beam is substantially parallel, but the laser output mirror 62 and the irradiation area 66 are conjugate with each other through an inclination correcting optical system and the two are in the relation of an object and an image and therefore, if the angle of the plane parallel plate 67 is changed, the position of the image, i.e., the laser beam application position, will parallel-move. Accordingly, by the angle of the plane parallel plate 67 being changed, the laser beam application position in the irradiation area 66 can be adjusted. Also, the plane parallel plate 67 is inserted in the portion wherein the laser beam is substantially parallel and therefore, even if the angle of the plane parallel plate 67 is changed, aberrations will not vary and no harmful ghost image will be created in the irradiation area 66. Further, generally the irradiation optical system is a reduction system and therefore, relative to any change in the angle of the plane parallel plate 67, any change in the laser beam application position at the irradiation position 66 is also reduced and thus, highly accurate alignment becomes possible. Moreover, in this direction, the irradiation optical system is an inclination correcting irradiation optical system and therefore, if the plane parallel plate 67 is once fixed, the laser beam application position will not change even if the pointing of the laser beam fluctuates.

As described above, the inclination correcting irradiation optical system is adopted as the irradiation optical system in the direction orthogonal to the flow path and further, the plane parallel plate of variable angle is inserted between the output mirror of the laser which is the light source and said irradiation optical system, whereby highly accurate alignment adjustment in the direction orthogonal to the flow path can be accomplished without creating aberrations and any harmful ghost image and moreover, if the plane parallel plate is fixed, there can be realized an irradiation optical system in which the laser beam application position will not fluctuate even if the pointing of the laser beam fluctuates. Moreover, even if the angle of the plane parallel plate is changed, the laser beam application position will not move in the direction parallel to the flow path and therefore, during alignment, any unintended change in the laser beam application position can be suppressed.

In the present embodiment, a plane parallel plate is employed as the displacing means, whereas this is not restrictive, but can be replaced by any element having an equivalent function.

What is claimed is:

1. A measuring apparatus comprising:
    an energy radiation source;
    applying means for applying radiation from said energy radiation source to an object to be examined, said object to be examined including particles flowing through a flow path; and
    detecting means for detecting a characteristic of said object to be examined;
    said applying means making a fulcrum of the fluctuation of the pointing of said radiation energy and an irradiation area in which said object to be examined is irradiated with the radiation energy substantially conjugate with each other;
    wherein the fulcrum of the fluctuation of the directionality of the radiation energy and the radiation area are made conjugate with each other in a direction crossing the flow direction of said path.

2. A measuring apparatus according to claim 1, wherein said applying means includes an anamorphic optical system.

3. A measuring apparatus according to claim 1, wherein said direction is orthogonal to the flow direction.

4. A measuring apparatus according to claim 1, further comprising displacing means disposed between said energy radiation source and said applying means for displacing the position of said radiation energy.

5. A measuring apparatus according to claim 1, wherein said energy radiation source includes a light source, and said radiation energy is light.

6. A measuring apparatus according to claim 5, wherein said light source includes a laser source.

7. A measuring apparatus according to claim 6, wherein the fulcrum of the fluctuation of the pointing of said radiation energy is near a laser output mirror, and the vicinity of said output mirror sand said irradiation area are made substantially conjugate with each other.

8. A measuring apparatus according to claim 6, wherein the beam waist of a laser beam is formed in said irradiation area.

9. A measuring apparatus according to claim 1, wherein the characteristic of said object to be examined is an optical characteristic including scattered light and/or fluorescence, and said detecting means includes a photodetector.

10. A measuring apparatus according to claim 1, wherein said particles are biological cells.

* * * * *

UNITED STATES PATENT AND TRADEMARK OFFICE
CERTIFICATE OF CORRECTION

PATENT No : 5,446,532

DATED : August 29, 1995

INVENTOR(S): TATSUYA YAMAZAKI

It is certified that error appears in the above-identified patent and that said Letters Patent is hereby corrected as shown below:

COLUMN 2

Line 52, "$z_0 = f$" should read --$z_0 = -f$--.

COLUMN 3

Line 67, "cell" should read --cell 5--.

COLUMN 8

Line 37, "radiation" should read --radiation energy--.

Signed and Sealed this

Twentieth Day of February, 1996

Attest:

BRUCE LEHMAN

Attesting Officer      Commissioner of Patents and Trademarks